United States Patent
Chaudhari et al.

(10) Patent No.: US 8,415,511 B2
(45) Date of Patent: Apr. 9, 2013

(54) POLYOL HYDROGENOLYSIS BY IN-SITU GENERATED HYDROGEN

(75) Inventors: Raghunath V. Chaudhari, Lawrence, KS (US); Debdut S. Roy, Lawrence, KS (US); Bala Subramaniam, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 259 days.

(21) Appl. No.: 12/796,245

(22) Filed: Jun. 8, 2010

(65) Prior Publication Data

US 2011/0004029 A1 Jan. 6, 2011

Related U.S. Application Data

(60) Provisional application No. 61/185,092, filed on Jun. 8, 2009.

(51) Int. Cl.
*C07C 29/60* (2006.01)
*B01J 23/42* (2006.01)
*B01J 23/46* (2006.01)
*B01J 31/02* (2006.01)

(52) U.S. Cl. ......... 568/861; 502/172; 502/332; 502/334

(58) Field of Classification Search .................. 568/861; 502/172, 332, 334
See application file for complete search history.

(56) References Cited

U.S. PATENT DOCUMENTS

| 5,326,912 | A | 7/1994 | Gubitosa et al. |
| 6,841,085 | B2 | 1/2005 | Werpy et al. |
| 2007/0078289 | A1* | 4/2007 | Xu et al. ............ 585/752 |
| 2008/0025903 | A1 | 1/2008 | Cortright |
| 2008/0103339 | A1 | 5/2008 | Bloom |

OTHER PUBLICATIONS

International Search Report dated Feb. 7, 2011 as issued in connection with corresponding PCT Application No. PCT/US2010/037774, filed on Jun. 8, 2010.

* cited by examiner

*Primary Examiner* — Sikarl Witherspoon
(74) *Attorney, Agent, or Firm* — Stinson Morrison Hecker LLP

(57) ABSTRACT

A catalyst composition/system can include: a platinum catalyst metal (Pt) and/or rhenium catalyst metal (Re) on a first support; and a ruthenium catalyst metal (Ru) and/or rhenium catalyst metal (Re) on a second support or a platinum catalyst metal (Pt) and a ruthenium catalyst metal (Ru) and/or a rhenium catalyst metal (Re) on the same support. The Pt:Ru, Re:Pt and/or Re:Ru weight ratio can be between about 1:4 and about 4:1. The support can be alumina, carbon, silica, a zeolite, $TiO_2$, $ZrO_2$ or another suitable material. The first and second support can be on the same support structure or on different support structures. In one option, the first and second supports can be positioned such that the Pt and/or Re are capable of catalyzing a dehydrogenation and/or reforming reaction that produces hydrogen and the Ru and/or Re are capable of catalyzing a hydrogenolysis reaction.

17 Claims, 5 Drawing Sheets

POLYOL HYDROGENOLYSIS BY IN-SITU GENERATED HYDROGEN

CROSS-REFERENCE

This patent application claims benefit of U.S. provisional patent application 61/185,092, filed Jun. 8, 2009, which provisional application is incorporated herein by specific reference in its entirety.

BACKGROUND

The increasing demand of fossil fuels, in view of limited supplies, has provided motivation to develop alternative resources and technologies for obtaining fuels and chemicals. Renewable resources that produce biomass materials are being investigated for use in conversion processes that can produce substances traditionally obtained from fossil fuels. For example, transesterification of vegetable oil based fatty acids to bio-diesel provides an example of a renewable resource that can be processed into a fuel. The current transesterification processes result in glycerol being formed as a side product (about 10% by wt.) during bio-diesel manufacture. Therefore, it would be advantageous to have an effective process for converting glycerol into a useful chemical. In addition, glycerol can also be produced in large quantities from various forms of biomass derived cellulosic materials

SUMMARY

In one embodiment, a catalytic system can include: a platinum metal (Pt) and/or rhenium metal (Re) on a first support; and a ruthenium metal (Ru) and/or rhenium metal (Re) on a second support, where Re is not alone on a support. Re alone has no activity as a catalyst in this reaction. Accordingly, the combinations can include Pt—Re:Ru, Pt:Ru, Pt:Re, and Re:Ru, and the Pt—Re:Ru, Pt:Ru, Re:Pt and/or Re:Ru weight ratio can be between about 1:4 and about 4:1. The support can be alumina, carbon, silica, a zeolite, $TiO_2$, $ZrO_2$ and materials thereof, or another suitable material. The first and second support can be on the same macro support structure or on different micro support structures. As such, the reforming catalyst (Pt and/or Re) can be on the same support together, and the hydrogenolysis catalyst (Re and/or Ru) can be on the same support together, and the reforming and hydrogenolysis catalysts (Pt—Re:Ru, Pt:Ru, Re:Pt and/or Re:Ru) can be on the same support together. In some instances, the individual catalyst metals can be on their own individual support. In one option, the first and second supports bearing different metals can be positioned such that the Pt and/or Re are in a position capable of catalyzing a dehydrogenation and/or reforming reaction that produces hydrogen and the Ru and/or Re are in a position capable of catalyzing a hydrogenolysis reaction.

In one embodiment, the catalytic system can be included in a reaction composition that has one or more of a polyol and/or water. Other solvents may be combined with water to form an aqueous liquid. In one aspect, the polyols can be selected from glycerol, glucose, sorbitol, mannitol, fructose, cellobiose, a polyhydroxy compound, or combinations thereof. The polyol content can range from about 0.001 to about 99.99% of the liquid phase composition exclusive of the catalyst, or from about 1% to about 99%, about 10% to about 90%, about 20% to about 80%, about 30% to about 70%, about 40% to about 60%, or about 50%. The reaction composition can be substantially devoid of externally added hydrogen. In situ generated hydrogen is preferable. As such, a polyol and/or dehydrogenation product thereof can be in the presence of in situ formed hydrogen and in the absence of externally added hydrogen. In one aspect, the reaction composition is a liquid.

In one embodiment, a catalytic system can include: a platinum metal (Pt) and rhenium metal (Re) on a first support; and a ruthenium metal (Ru) on a second support.

In one embodiment, a catalytic system can include: a platinum metal (Pt) on a first support; and a ruthenium metal (Ru) and rhenium metal (Re) on a second support.

In one embodiment, a platinum metal (Pt), rhenium metal (Re), and ruthenium metal (Ru) are on the same support.

In one aspect, the first, second supports are each on different macroscopic support structures. In another aspect, the first and second supports are each on the same macro support structure.

In one aspect, the first and second supports are each made of a different material. In another aspect, the first and second supports are both made of the same material.

A hydrogenolysis process can include: providing the catalytic system as described herein; reacting a polyol with the catalytic system to produce hydrogen and form a dehydrogenated polyol product; and reacting the hydrogen and the dehydrogenated polyol product and/or second polyol with the catalytic system to form an alcohol or lower polyol. In one aspect, the process can be conducted with the catalytic system held at a temperature of 180° C. to 250° C., and/or at a pressure of 10 bar to 15 bar (in inert nitrogen atmosphere or autogenous pressure condition). In another aspect, the reaction includes the catalytic system being in a liquid, and the reactions occur in the liquid. As such, the solid catalyst is in contact with a liquid either as a packing or a suspension and the reactions occur in the liquid. In another aspect, the reaction occurs without external hydrogen. In another aspect, the conversion of polyol to alcohol or lower polyol ranges from about 20% to about 83%. In another aspect, the selectivity to reaction product alcohol and lower polyol ranges from about 26 mole % to about 53 mole % for 1,2-propanediol and about 2.5 mole % to about 9 mole % for ethylene glycol and about 0 mole % to about 2 mole % for ethanol when the polyol is glycerol.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
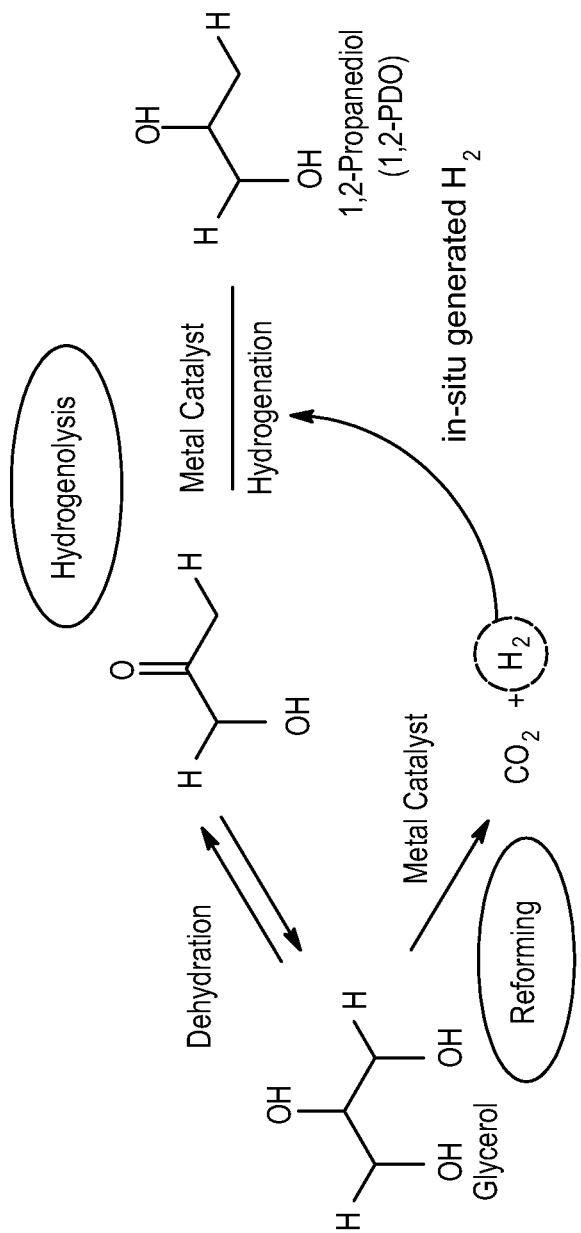
FIG. 1 includes a schematic representation of in situ generated hydrogen and utilizing the hydrogen for glycerol hydrogenolysis to 1,2-propanediol.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Generally, the present invention is related to catalytic compositions, systems, and methods for hydrogenolysis of polyols without using externally added hydrogen. Accordingly, the present invention includes combination catalysts, such as various combinations of platinum metal (Pt), rhenium metal (Re), and a ruthenium metal (Ru). This can include Pt and Ru; Re and Ru; or Pt, Re, and Ru combinations, where the different metal types are on separate supports or combined as two or three catalytic metals on the same support structure. The catalytic system can include the different catalytic metals being bound to the same support, or bound to different supports that are then combined to form an admixture catalyst system.

In one embodiment, a catalyst system can include a physical mixture of a Pt and/or Re catalyst on a support and a Ru and/or Re catalyst on a support. The supports may be the same or different. The Pt:Ru, Re:Ru, and/or Pt—Re:Ru weight ratio can be between about 1:4 and 4:1, more preferably between about 1:3 and 3:1, more preferably between about 1:2 and 2:1, and most preferably about 1:1. In one aspect, the ratio of Pt and/or Re catalyst with Ru catalyst is about 1:1. It has been found that selectivity for 1,2-PDO is highest with a 1:1 catalyst composition.

In one embodiment, the support is either alumina, or carbon, or silica, or a zeolite, $TiO_2$, $ZrO_2$ or another suitable material. The same or different material can be used for the support for each catalyst. Also, the different catalysts may be coupled to the same support structure, such as a macro support structure.

The catalytic system can be used for hydrogenolysis of various polyols to alcohols or lower alcohols without any external hydrogen being added. Traditionally, external hydrogen is introduced into a reaction mixture to facilitate hydrogenolysis. Now, a reforming catalyst, such as Pt or Pt—Re, can be used for producing in situ hydrogen, where the in situ hydrogen further reacts with either the polyol and/or polyol dehydrogenation product to produce lower polyol that has less hydroxyl groups.

The polyol reactant has more hydroxyl groups than the hydrogenolysis product. As such, the reactant polyol can be a "higher polyol" that has a higher number of hydroxyl groups compared to the reaction product that is an alcohol (e.g., single hydroxyl) or "lower polyol" that has a lower number of hydroxyl groups compared to the reactant polyol. For example, the hydrogenolysis of a polyol reactant can result in a hydrogenolysis product that is a lower polyol having one less hydroxyl group or two or more fewer hydroxyl groups. In a specific example, the catalysts can facilitate hydrogenolysis of glycerol to produce 1,2-propanediol (1,2-PDO), which shows that hydrogenolysis reduces a triol to a diol (FIG. 1).

Figure 3:
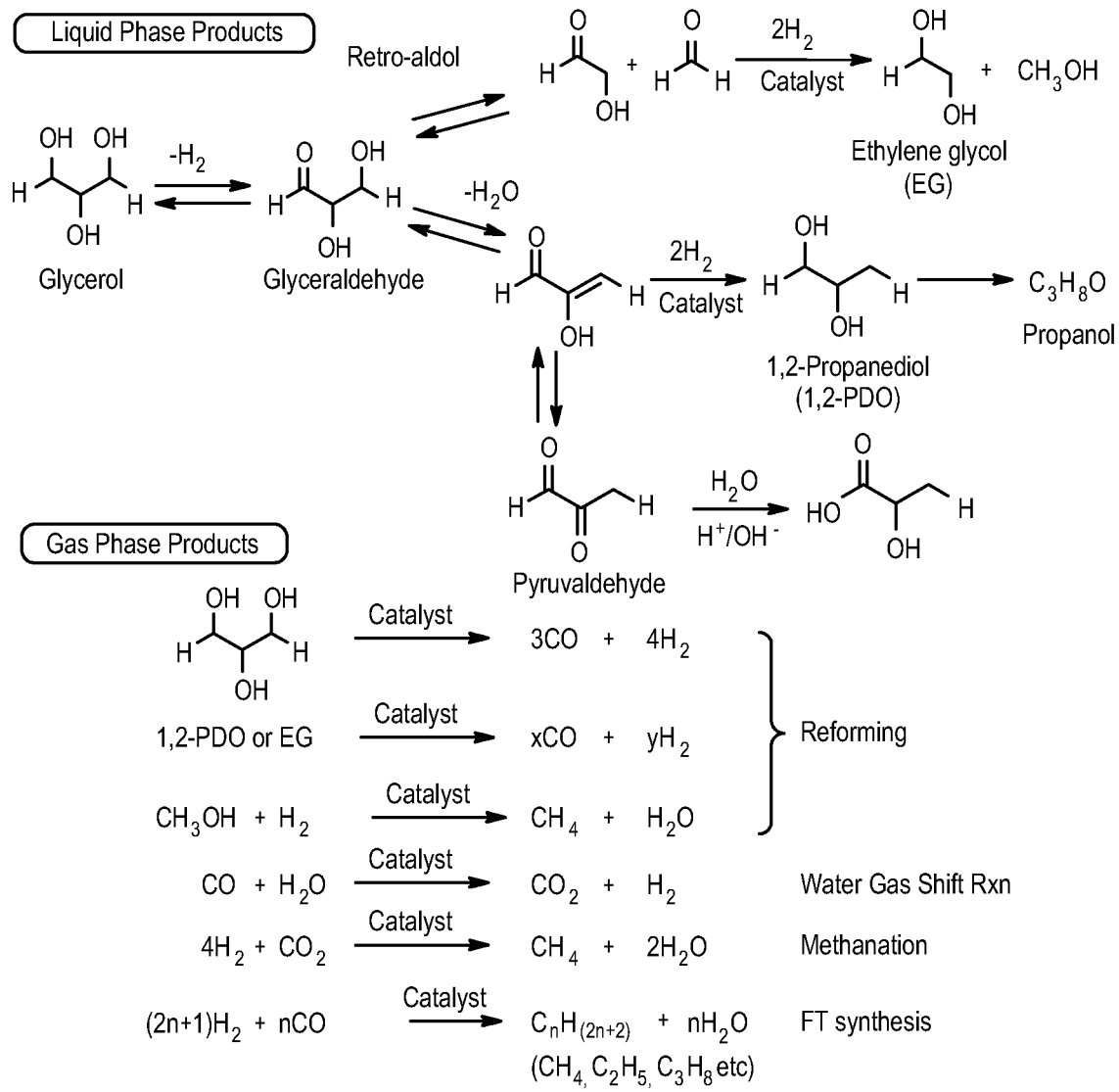
FIG. 3 includes a schematic representation of liquid phase and gas phase reactions and products that may be possible.

Accordingly, the present invention can include using the catalytic system in a hydrogenolysis process for converting polyols in an aqueous phase to lower oxygenated compounds without any external hydrogen being added. The catalytic system produces the hydrogen from the polyol for the hydrogenolysis reaction. Part of the polyol reactant produces hydrogen in situ by aqueous reforming under the reaction conditions. The in situ produced hydrogen participates in the hydrogenolysis reaction of the remaining polyol or polyol dehydrogenation product to yield lower deoxygenated products. The polyol dehydrogenation product can be formed when hydrogen is removed by the catalyst system. By eliminating the need for hydrogen to be added to the reaction, and thereby eliminating a hydrogen feed into the reactor, the process can be operated at a lower pressure (e.g., about 10-20 times lower pressure compared to when external hydrogen is introduced), which improves the economics and safety of the process. Further, by limiting the availability of excess hydrogen, the inventive process (without externally added hydrogen) improves the product selectivity when compared to current processes with external hydrogen addition. Also, when there is no externally added hydrogen, there may be less hydrogen in the gas phase, which can reduce the formation of undesirable side products as shown in FIG. 3.

The hydrogenolysis process with in situ generated hydrogen results in high conversion for glycerol (e.g., about 50.1%) and high selectivity to desired deoxygenated products (e.g., 1,2-propanediol when glycerol is the reactant: selectivity is about 47.2%) without adding hydrogen from an external source. In the absence of externally added hydrogen, the catalyst combination performed in a superior manner when compared to experiments with added hydrogen (e.g., when partial pressure of hydrogen was 41 bar) in selectivity with 47.2% and 31.9%, respectively. This self-sustainable process utilizes part of the polyol to generate hydrogen due to the supported Pt and/or Re catalyst, and the hydrogen is then used for hydrogenolysis of either the remaining polyol and/or polyol dehydrogenation product by supported Ru and/or Re catalyst.

The process is surprisingly and unexpectedly improved by limiting or reducing excess hydrogen availability in the reaction, and thereby reduces side reactions. The process can also be operated at lower pressures compared to the experiments with externally added hydrogen with improved performance and polyol conversion. The process generates hydrogen from the polyol feed, and reduces undesired side reactions in polyol hydrogenolysis reactions. Some of the advantages in the process are as follows: (a) no need of external hydrogen addition; (b) reaction can start at ambient pressure which improves process safety; (c) renewable and cheap polyols can be used as a hydrogen source; and (d) better productivity of the process with respect to yields and polyol utilization to useful products by increased selectivity. Additional environmental benefit can be realized when the reactant polyols are produced from converted biomass. The bio-based polyols can then be processed into industrial chemicals, some examples of which are products such as 1,2 propanediol, ethylene glycol, n-propanol, and others from glycerol, sorbitol, xylitol and the like. Different reactant polyols can produce different types of chemical products.

In the experiments described herein, it was found that the catalyst combination can produce hydrogen in situ, and hydrogenolysis of the polyol can be conducted with the in situ generated hydrogen. A particular example can now be described. Aqueous phase hydrogenolysis of glycerol to 1,2-propanediol (1,2-PDO) can be catalyzed by an admixture of 5 wt. % $Ru/Al_2O_3$ and 5 wt. % $Pt/Al_2O_3$ catalysts in varying amounts, without externally added hydrogen. Favorable conversion is obtained in the liquid phase. The hydrogen generated in situ by aqueous phase reforming of glycerol can be used for the conversion of glycerol to 1,2-PDO and other products as shown in FIG. 3.

During 6 hour batch runs described in more detail below, it was observed that the 1:1 admixture (by weight) of the Ru and Pt catalysts showed better performance at about 220° C. (493 K) [glycerol conversion (X)=50.1%, 1,2-PDO selectivity (S)=47.2%] compared to the individual catalysts [X=19.3%, S=50% with 5% $Ru/Al_2O_3$; X=18.1%, S=37% with 5% $Pt/Al_2O_3$]. A run for glycerol hydrogenolysis with the admixture catalyst in the presence of added hydrogen (41 bar), at otherwise identical operating conditions, showed lower selectivity to 1,2-PDO (31.9%) compared to the run without added hydrogen (47.2%). With external hydrogen addition, the availability of excess hydrogen (in addition of the in situ hydrogen generation) unfavorably promotes the transformation of CO and $CO_2$ to methane and other alkanes, adversely affecting the 1,2-PDO selectivity.

The effect of temperature on glycerol hydrogenolysis with the Pt—Ru admixture catalyst in the absence of externally added hydrogen showed an increase in glycerol conversion from 20.6% to 82.6% in the temperature range of about 200° C. to about 250° C. (473 K to 523 K) and a steady decrease in selectivity of 1,2-PDO from 53.1% to 26.5%. The decrease in 1,2-PDO selectivity was attributed to higher reforming rate of 1,2-PDO and increased methanation rate which decreased hydrogen availability for hydrogenolysis at higher temperature.

Based on detailed characterization of both liquid phase and gas phase products, we have demonstrated that aqueous phase hydrogenolysis of abundantly available and renewable glycerol feedstock with a admixture catalyst system having a reforming (Pt) and a hydrogenolysis catalyst (Ru) and without external hydrogen addition can be used for producing 1,2-propanediol. The hydrogen generated from aqueous phase reforming of glycerol is used for simultaneous hydrogenolysis of remaining glycerol to 1,2-PDO. The fact that the hydrogen is derived from part of the feedstock obviates the need for external hydrogen addition. Most significantly, the admixture catalyst showed synergistic effect over individual metal components providing better selectivity to the hydrogenolysis product (1,2-PDO) without external hydrogen addition. The admixture catalyst showed very good stability during several recycle runs. The proposed strategy can also be applied for hydrogenolysis of other polyols to value added chemicals and indicates a potential to design bimetallic catalysts for the combo reforming-hydrogenolysis reactions.

In one embodiment, the hydrogenolysis conversion of polyol can range from about 15% to about 90%, about 20% to 83%, or 30% to about 53% (molar). In one aspect, selectivity to liquid products associated with the conversion can range from about 26 to 53 mole % for 1,2-propanediol and 2.5 to 9 mole % for ethylene glycol and 0 to 2 mole % for ethanol based on converted glycerol. The observed conversion and selectivity are better than the sums of these quantities observed when each of the catalytic material exists solely by itself on different supports in identical relative amounts.

In one embodiment, the hydrogenolysis of polyols is carried out at greater than about 200° C. ($\geqq$473 K), wherein polyol reforming is quite significant to produce hydrogen. In one aspect, the yield of 1,2-PDO is optimized by reaction at about 220° C. (493 K).

In one embodiment, a reaction mixture can be a liquid phase composition that includes a polyol, water, and the catalyst combination. In one aspect, the polyol can be selected from glycerol, glucose, sorbitol, mannitol, fructose, cellobiose, or any polyhydroxy compound.

In another aspect, the polyol content can range from 1 to 100% by weight or volume of the liquid phase composition, or from about 0.001 to about 99.99% of the liquid phase composition exclusive of the catalyst, or from about 1% to about 99%, about 10% to about 90%, about 20% to about 80%, about 30% to about 70%, about 40% to about 60%, or about 50%.

The catalyst particles may be either suspended in a liquid phase as particles or packed in a tube through which the reactants (e.g., substrate dissolved in solution and gas) are passed. The reaction occurs on catalytically active metal sites on the surface of the catalyst in the presence of the substrate.

In one embodiment, the catalyst combinations can be used in a similar reaction protocol where the polyols are substituted with carboxylic acids. The carboxylic acids can then be converted catalytically to produce in situ hydrogen, and further to the hydrogenolysis products.

In one embodiment, the catalyst combinations can be used in a reaction protocol with the reactant being biomass, derivatized biomass, or partially-processed biomass to result in polyols and carboxylic acids. The obtained polyols and carboxylic acids can then be further reacted through catalyzed reforming with in situ hydrogen generation and catalyzed hydrogenolysis with the in situ hydrogen. Suitable biomass products or starting reagents for conversion to chemicals and fuels can include succinic acid, 2,5-furandicarboxylic acid, 3-hydroxypropionic acid, aspartic acid, glucaric acid, glutamic acid, itaconic acid, levulinic acid, 3-hydroxybutyrolactone, glycerol, sorbitol, xylitol, or the like.

In one embodiment, the reaction mixture can be held at a temperature of about 100° C. to 300° C., more preferably 180° C. to 250° C., and more preferably 200° C. to 225° C. to conduct the hydrogenolysis. The hydrogenolysis can be conducted with or without externally added hydrogen. As described herein, it can be preferable that no external hydrogen is added, however, a small and insignificant amount of external hydrogen can be added such that the reaction is conducted substantially devoid of externally added hydrogen.

In one aspect, the process can be conducted with the catalytic system held at a pressure of about 5 bar to about 25 bar, about 10 bar to 20 bar, or about 12 bar to 15 bar. These lower pressure ranges are economically beneficial. However, higher pressures can, of course, be used.

In one embodiment, the hydrogenolysis reaction products can be used in various industries. For example, the products can be used in a moisturizer, antifreeze, and de-icing products.

EXAMPLES

Glycerol ($\geqq$99.5%, spectrophotometric grade) was purchased from Sigma Aldrich and used without further purification. The 5% $Ru/Al_2O_3$ and 5% $Pt/Al_2O_3$ catalysts were purchased from Sigma Aldrich and used as received. The 5% $Ru/Al_2O_3$ and 5% $Pt/Al_2O_3$ catalysts were in powder form with particle size ranging from 75-150 µm and 100-125 µm, respectively. Hydrogen (purity >99.5%) and Nitrogen (purity >99%) were procured from Air Gas Inc. and Linweld, respectively, and used as received.

Figure 2:
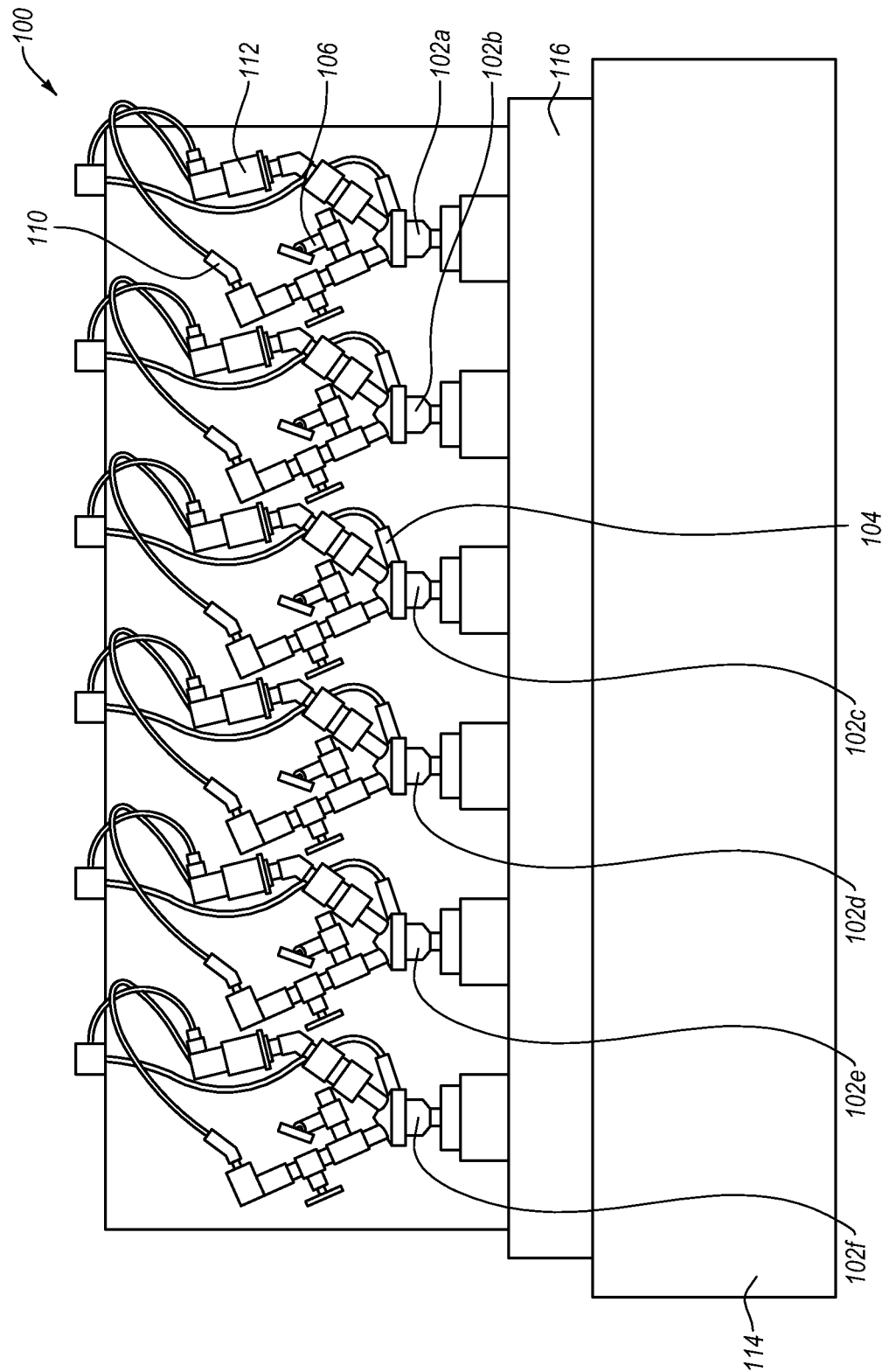
FIG. 2 includes a schematic representation of an embodiment of a multiple slurry reactor system.

The catalytic hydrogenolysis of glycerol was carried out in a high pressure, high temperature multiple slurry reactor system 100 (FIG. 2) supplied by Parr Instrument Co., Moline, Ala. The reactor system 100 includes a parallel array of six autoclave reactors 102a-f that can be operated simultaneously at different temperatures and pressures. Each autoclave reactor 102 is equipped with a thermowell 104, gas outlet 106, gas inlet 110, and a pressure transducer 112. Also, the reactor system includes a rupture disc, although it is not visible in the figure. The rupture disc can be important in a high pressure reactor. A magnetic stirrer system 114 with maximum agitation speed of 30 Hz provides mixing in each reactor 102. The temperatures and pressures in the individual reactors 102 are independently controlled and monitored with a computer (not shown) interfaced with the control module 116 of the reactor system 100. The common agitation speeds of the reactors 102 can be controlled from the computer interface or with the manual controller (not shown) in the reactor setup itself. The temperature and pressure of the reactors 102 as well as the hydrogen are logged every 5 seconds through SpecView data acquisition software.

In a typical hydrogenolysis experiment, a known amount of glycerol dissolved in water is charged into the reactor. An initial sample is collected at that condition. Predetermined amounts of the 5% $Pt/Al_2O_3$ and 5% $Ru/Al_2O_3$ catalysts, either alone or a mixture of the two, are then charged into the reactor and the reactor is sealed. The other reactors are charged in a similar manner. The reactors are placed into the heating slots of the multiple reactor assembly and then purged 2-3 times with $N_2$ at room temperature. The reactors are heated to a desired temperature under low agitation speed (3-4 Hz). After attaining the desired temperature, $N_2$ is introduced into the reactor to make up the pressure to 14 bar; the agitator speed is increased to 25 Hz and the reactions allowed to proceed. The $N_2$ pressurization allows easy and adequate sampling of the gas phase for GC analysis at the end of the run. Following a predetermined batch reaction time, the reactors are allowed to cool down to room temperature. The gas phase samples are analyzed by GC (Shimadzu GC 2014). In one sampling loop, $H_2$, CO, $CO_2$, methane and methanol are analyzed using a 60/80 Carboxen 1000 column (packing material: carbon molecular sieve; 4.5 m×2.1 mm×0.50 µm film thickness) connected to a thermal conductivity detector (TCD). In another loop, $C_1$-$C_5$ alkanes are analyzed using a Hayesep DB (packing material: Divinylbenzene; 2.5 m×3.1 mm×0.25 µm film thickness) column and a flame ionization detector (FID). The liquid samples are analyzed by HPLC (Shimadzu) using a Rezex ROA-Organic Acid H+ (8%) column (300×7.8 mm), 0.005 N aqueous $H_2SO_4$ as mobile phase and a refractive index detector (RID). The analytical results from the HPLC and GC are combined to get a quantitative assessment of each product (in the gas and liquid phases) and to calculate the glycerol conversion and product selectivity. In all the runs, the analytical procedure is able to account for >90% of the starting glycerol.

The influence of $N_2$ pressure on activity and product selectivity was studied (Table 1). The results indicate that the $H_2$ is generated in situ from aqueous phase reforming (dehydrogenation) of glycerol. The glycerol subsequently reacts with the remaining glycerol to produce 1,2-PDO and other products, and is unaffected by the $N_2$ pressure. We employed 14 bar of $N_2$ in all the experiments to provide adequate gas phase samples for analysis.

TABLE 1

Effect of $N_2$ pressure on glycerol hydrogenolysis without external $H_2$ addition

| $P_{N2}$ | 0 bar | 14 bar | 41 bar |
|---|---|---|---|
| Glycerol Conversion, % | 43.2 | 50.2 | 42.8 |
| Liquid phase product selectivity, % | | | |
| EG | 7.2 | 6.3 | 7.5 |
| 1,2-PDO | 48.7 | 47.2 | 45.8 |
| Glyceraldehyde | 0 | 0 | 0.01 |
| Lactic acid | 1.9 | 1.6 | 1.3 |
| MeOH | 0 | 0.3 | 0.03 |
| EtOH | 3.9 | 1.1 | 3.82 |
| Gas phase product selectivity, % | | | |
| Methane | 17.4 | 18.3 | 12.9 |
| Ethane | 1.6 | 0.9 | 0.9 |
| Propane | 0.6 | 0.4 | 0.5 |
| n-Butane | 0.1 | 1.2 | 0.1 |
| n-Pentane | 0.6 | 0.6 | 0.5 |
| CO | 0.43 | 1.3 | 0.8 |
| $CO_2$ | 9.8 | 14.3 | 15.1 |
| C deficit, % | 5.3 | 3.8 | 4.5 |

Reaction conditions:
Glycerol: 3 g,
5% $Ru/Al_2O_3$: 0.125 g,
5% $Pt/Al_2O_3$: 0.125 g, 493 K;
Solvent: $H_2O$;
Initial liquid volume: 30 mL;
Batch reaction time: 6 h An admixture of catalysts having various weight ratios of 5% $Ru/Al_2O_3$ and 5% $Pt/Al_2O_3$ were used. For clarity, the quantities of supported Ru and Pt catalysts used in each admixture of catalyst are shown in Table 2.

TABLE 2

Composition of admixture Ru:Pt catalysts

| Ru:Pt catalyst wt ratio | 5% $Ru/Al_2O_3$, g | 5% $Pt/Al_2O_3$, g |
|---|---|---|
| 0.5:1 | 0.0625 | 0.125 |
| 1:1 | 0.125 | 0.125 |
| 2:1 | 0.250 | 0.125 |
| 4:1 | 0.500 | 0.125 |
| 1:2 | 0.125 | 0.250 |

For catalyst recycling studies, the reactor content following a run was transferred into a centrifugation tube using a pipette. The solid phase, containing the $Ru/Al_2O_3$ and $Pt/Al_2O_3$ admixture, was separated from the liquid phase by centrifugation. The liquid phase at the top was pipetted out carefully. The wet solid was then washed with water and separated from the catalyst. This washing and filtering procedure was repeated 3-4 times to remove any remaining adsorbed organic species from the catalyst surface. A fresh charge of the required amount of glycerol dissolved in water was used to transfer the solid from the centrifuge tube to the reactor for a recycle run. After three such recycle runs, the catalyst was separated from the liquid phase, washed with water as described above, and then centrifuged a few times with added acetone to replace traces of water adsorbed on the catalyst. The catalyst was then dried under flowing nitrogen first and then in a furnace at about 100° C. (373 K) under nitrogen flow. The surface areas of the fresh and recovered catalysts were measured using a Gemini 2360 surface area analyzer (Micromeritics).

The glycerol conversion is defined as the ratio of the moles of glycerol consumed during the reaction to the moles of glycerol charged initially expressed as percentage. Selectivity to a particular product is defined as the ratio of carbon in a particular product to the total carbon in all products also expressed as percentage. In other words, the carbon-based selectivity defined above considered the products in the liquid phase as well as in the gas phase. It is well known that CO, $CO_2$ and methane can form with this class of catalytic reaction, as confirmed in our present study. Clearly therefore, the selectivity based on considering liquid phase products alone are not the intrinsic values and are always overestimated. The analytical protocol described above was developed to provide complete analysis of liquid as well as gas phase products in order to quantify them and the extent of material balance closure. The percentage difference in the measured molar carbon content in the feed and product streams, relative to the feed stream, is termed as the 'carbon deficit'.

$$\text{Carbon deficit} = \frac{100 \times (C_{feed} - C_{unreacted\ glycerol + products})}{C_{feed}} \%$$

A typical material balance analysis showing quantities of the detected liquid phase and gas phase products is shown in Table 3.

TABLE 3

Typical material balance sheet for glycerol hydrogenolysis

| Final sample: | Conc., kmol/m$^3$ | C moles (×10$^3$) | % |
|---|---|---|---|
| Liquid phase components | | | |
| | | | Conversion |
| Glycerol: | 0.541 | 48.69 | 50.09 |
| | | | Selectivity |
| Ethylene glycol (EG): | 0.051 | 3.06 | 6.26 |
| 1,2-propanediol (1,2-PDO): | 0.257 | 23.13 | 47.33 |
| 1,3-propanediol (1,3-PDO): | 0 | 0 | 0.00 |
| Glyceraldehyde | 0 | 0 | 0.00 |
| Lactic acid: | 0.009 | 0.81 | 1.66 |
| Oxalic acid: | 0 | 0 | 0.00 |
| Ethanol: | 0.009 | 0.54 | 1.10 |
| 2-Propanol: | 0 | 0 | 0.00 |
| 1-Propanol: | 0 | 0 | 0.00 |
| Methanol: | 0.002 | 0.07 | 0.14 |
| Gas phase components | | | |
| Methane: | 0.129 | 9.02 | 18.46 |
| Ethane: | 0.003 | 0.43 | 0.87 |
| Propane: | 9.4 × 10$^{-4}$ | 0.19 | 0.41 |
| Methanol: | 9.6 × 10$^{-4}$ | 0.01 | 0.14 |
| CO: | 0.009 | 0.66 | 1.35 |
| $CO_2$: | 0.101 | 7.04 | 14.40 |
| n-butane: | 0.002 | 0.62 | 1.26 |
| n-pentane: | 9.3 × 10$^{-4}$ | 0.33 | 0.67 |
| Totals: | | 94.65 | 94.05 |
| C Deficit: | 2.98% | | |

Initial:
Glycerol: 1.084 kmol/m$^3$ = 97.56 × 10$^{-3}$ moles of C
Hydrogenolysis Reaction conditions:
Glycerol: 2.992 g,
5% Ru/Al$_2$O$_3$: 0.125 g,
5% Pt/Al$_2$O$_3$: 0.125 g,
Temp.: 493 K,
$P_{N2}$: 14 bar,
Solvent: H$_2$O,
Initial liquid volume: 30 mL;
Batch time: 6 h.

Glycerol hydrogenolysis involves several consecutive as well as parallel reactions, and the product profile strongly depends upon the catalyst, promoters and reaction conditions. To understand the reaction network involved in glycerol hydrogenolysis, published literature information was used as guidance (FIG. 3). In addition, we conducted several diagnostic experiments to test the significance of side reactions on intermediate products under different conditions to confirm and better discern plausible reaction pathways. For example, glyceraldehyde at lower concentrations was identified in a few of our hydrogenolysis reactions. Glyceraldehyde can form by dehydrogenation of glycerol on the metal surface. It has been suggested that ethylene glycol (EG) and 1,2-PDO form from glyceraldehyde. Also, the retro-aldol reaction and the dehydration step may occur on a catalyst surface in absence of either an acidic or a basic promoter. It was reported that lactic acid forms during glycerol hydrogenolysis reaction via the glyceraldehyde and pyruvaldehyde intermediates in the presence of either an acidic or a basic promoter. However, we found lactic acid formation (selectivity: 1-4%) in all the experiments involving in situ hydrogen generation. A possible explanation is that $CO_2$ formed during the aqueous phase reforming of glycerol dissolves in the aqueous phase to generate carbonic acid ($H_2CO_3$), which upon dissociation can produce a free proton that promotes the transformation of pyruvaldehyde to lactic acid.

Diagnostic experiments with the individual liquid phase products of glycerol hydrogenolysis revealed that all the products (including methanol) undergo reforming at the experimental conditions (200° C. to 250° C. (473-523 K); 14 bar $N_2$ initial pressure). Methanol reforming to methane was observed with and without externally added hydrogen. Though methane was the major product from methanol when hydrogen was added from external sources, $CO_2$ was the major product (60% with 20% $CH_4$) in experiments without added hydrogen.

In another experiment with CO and added hydrogen in the presence of a Ru/Al$_2$O$_3$ catalyst, we found alkanes such as methane and ethane as products. However, a similar experiment with $CO_2$ and hydrogen produced only methane. Based on the literature data and our diagnostic experiments, possible reaction pathways involved in glycerol hydrogenolysis are shown in FIG. 3.

Ru—Pt catalyst combination generated hydrogen in situ from aqueous phase reforming of glycerol (e.g., dehydrogenation) and utilized the in situ hydrogen for hydrogenolysis of the remaining glycerol. Specifically, the following investigations were performed: (a) comparison of individual catalysts with the admixture catalyst under conditions of no external hydrogen addition; (b) effect of catalyst (Ru/Al$_2$O$_3$ and Pt/Al$_2$O$_3$) weight ratio on activity and selectivity of products in glycerol hydrogenolysis in absence of added hydrogen; (c) temperature effect; (d) catalyst performance comparison of the admixture with and without added hydrogen for glycerol hydrogenolysis, and (e) stability of the admixture catalyst during recycle runs.

The results with 5% Ru/Al$_2$O$_3$ and 5% Pt/Al$_2$O$_3$ admixture combinations and the monometallic catalysts on glycerol hydrogenolysis in absence of externally added hydrogen at about 220° C. (493 K) are compared in FIG. 4. The reaction conditions were as follows: glycerol at 3 g, total catalyst at 0.25 g, temperature at 220° C. (493 K), $P_{N2}$ at 14 bar, solvent was H$_2$O, initial liquid volume at 30 mL, and batch reaction time at 6 h.

Figure 4:
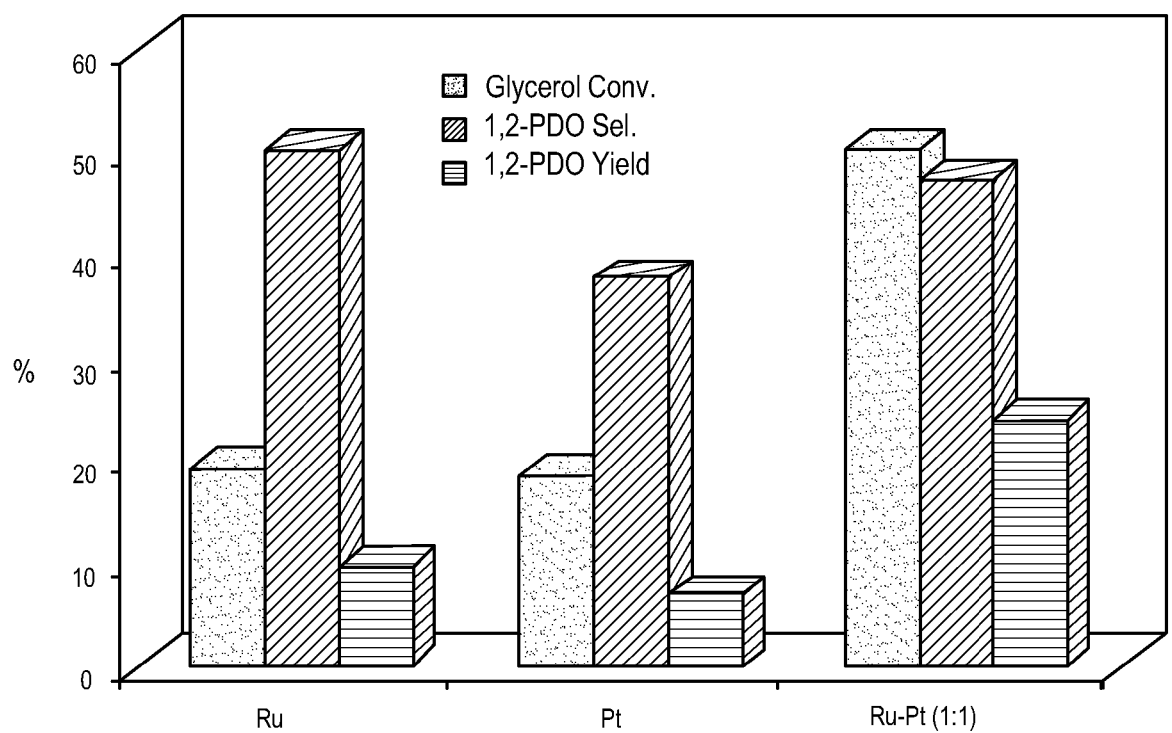
FIG. 4 includes a graph that shows the effect of Ru, Pt and Ru—Pt admixture catalysts on glycerol hydrogenolysis in the absence of externally added hydrogen.

It is evident from FIG. 4 that 1:1 (wt/wt) Ru—Pt admixture catalyst combination displays a positive synergy in improving the yield of 1,2-PDO compared to the monometallic catalysts. That is, the Ru—Pt admixture produced a synergistic yield over the additive amounts of Ru and Pt individually. Though the glycerol conversion was similar (~20%), the 5% Ru/Al$_2$O$_3$ catalyst gave higher selectivity to 1,2-PDO (50.1%) compared to the 5% Pt/Al$_2$O$_3$ catalyst (37.2%). The lower 1,2-PDO selectivity with Pt/Al$_2$O$_3$ catalyst is attributed to the higher reforming activity (e.g., dehydrogenation of the polyol) of Pt catalysts over hydrogenolysis reaction compared to Ru catalysts. Ru is a more effective hydrogenolysis catalyst. For the same overall loading of the admixture catalyst with equal weights of the Pt and Ru catalysts, significant improvement in glycerol conversion (50.2%) is noted while retaining high 1,2-PDO selectivity (47.1%). The fact that the glycerol conversion with the admixture catalyst is more than twice the value achieved with an identical amount of either the Pt or the Ru catalyst confirms a beneficial synergistic effect between Pt and Ru in the admixture catalyst.

Figure 5:
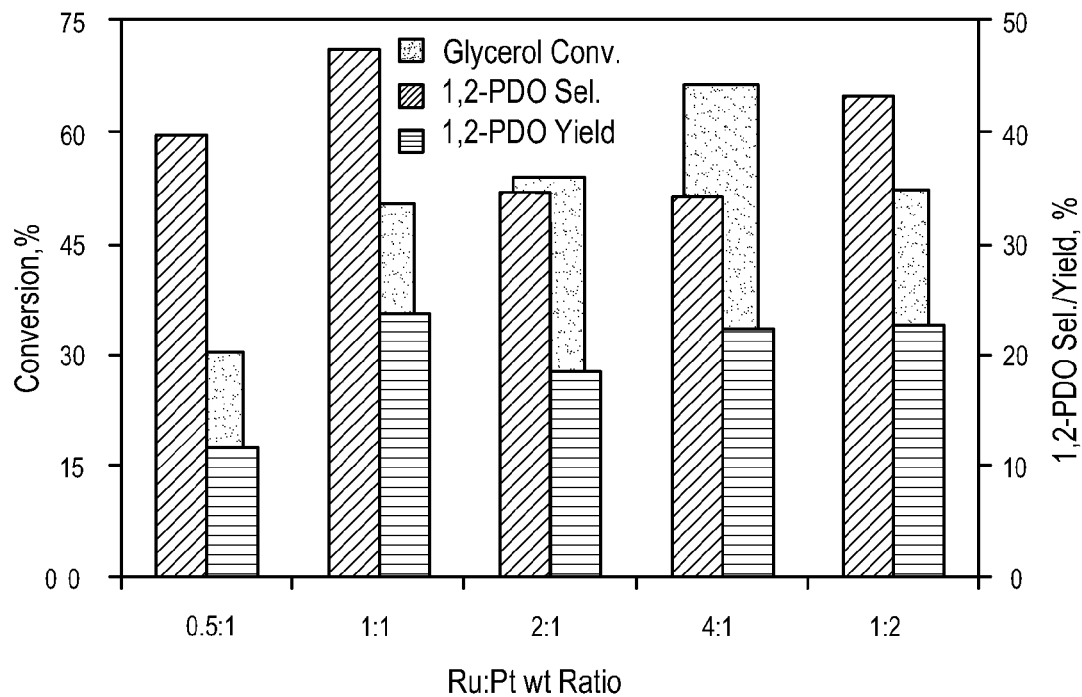
FIG. 5 includes a graph that shows the effect of Ru and Pt weight ratio on glycerol hydrogenolysis in the absence of externally added hydrogen.

The effect of the relative amounts of Ru and Pt content in the admixture was studied and the results are shown in FIG. 5. The amounts of the individual catalysts (5% Ru/Al$_2$O$_3$ and 5% Pt/Al$_2$O$_3$) used in various Ru:Pt admixtures studies are shown in Table 2. Glycerol conversion improved as the Ru:Pt ratio in the admixture is increased from 0.5:1 to 4:1 (30.2% to 65.8%).

Interestingly, the liquid phase concentration of 1,2-PDO in runs with 1:1 and 4:1 Ru:Pt admixture catalysts was very similar (0.253 and 0.245 kmol/m$^3$ respectively) although the glycerol conversion was higher in the latter case (65.8% for 4:1 Ru:Pt compared to 50.2% for 1:1 admixture). This indicates that the hydrogen available for hydrogenolysis reactions were similar in the two cases. Given that the amount of Pt/Al$_2$O$_3$ catalyst was identical (0.125 g) in these two cases, this further suggests that the hydrogen generated in situ is mainly due to the Pt catalyst. This is supported by the data obtained from the run with a 1:2 Ru—Pt catalyst admixture (containing 0.125 g of 5% Ru/Al$_2$O$_3$ and 0.250 g of 5% Pt/Al$_2$O$_3$), where 1,2-PDO selectivity improved with respect to 2:1 Ru—Pt catalyst admixture (containing 0.250 g of 5% Ru/Al$_2$O$_3$ and 0.125 g of 5% Pt/Al$_2$O$_3$) for nearly the same glycerol conversion. Further, the marginally lower 1,2-PDO selectivity with the 1:2 Ru:Pt admixture compared to 1:1 Ru:Pt admixture at nearly identical conversions indicates the absence of hydrogen starvation for hydrogenolysis even with the lower amount of Pt/Al$_2$O$_3$ in the 1:1 Ru:Pt admixture. This is in sharp contrast with the results obtained with 2:1 and 4:1 Ru:Pt admixture catalysts, wherein increasing amounts of Ru/Al$_2$O$_3$ at a fixed loading of Pt/Al$_2$O$_3$ (0.125 g) resulted in hydrogen starvation as inferred from the lower 1,2-PDO selectivity.

Ru is known to convert CO$_2$ to methane, and increasing Ru content in the admixture catalysts provides for more CO, CO$_2$ and hydrogen being consumed to form methane and other alkanes (methane selectivity: 18.3, 22.9 and 22.0% with 1:1, 2:1 and 4:1 Ru—Pt admixture catalysts, respectively). These results indicate that reactions involving CO and CO$_2$ with H$_2$ occur simultaneously with the hydrogenolysis reaction. From the foregoing results and discussion, we conclude that an increase in Ru content with respect to Pt, with no external hydrogen addition, has no beneficial effect on the overall productivity of 1,2-PDO and that the 1:1 Ru/Al$_2$O$_3$:Pt/Al$_2$O$_3$ admixture catalyst provides an optimum glycerol conversion and 1,2-PDO selectivity.

Temperature effects on glycerol conversion and 1,2-PDO selectivity in the 200° C. to 250° C. (473-523 K) range are summarized in Table 4. Glycerol conversion increased from 20.6% at 200° C. (473 K) to 82.6% at 250° C. (523 K); however, 1,2-PDO selectivity decreased steadily from 53.1% to 26.5%. The decrease in 1,2-PDO selectivity with temperature is attributed to the higher reforming rate of hydrogenolysis products (for example 1,2-PDO) at higher reaction temperature. The increased methane yield in the gas phase at higher temperatures indicates enhanced methanation activity that further reduces hydrogen availability for the hydrogenolysis reaction. As expected, the total yield of liquid phase products decreased at higher temperatures.

TABLE 4

Effect of temperature on glycerol hydrogenolysis without external H$_2$ addition

| | Temperature, K | | | |
|---|---|---|---|---|
| | 473 | 493 | 513 | 523 |
| Liquid phase product selectivity, % | | | | |
| Glycerol Conversion, % | 20.6 | 50.2 | 65.8 | 82.6 |
| EG | 8.9 | 6.26 | 2.7 | 2.6 |
| 1,2-PDO | 53.1 | 47.2 | 30.4 | 26.5 |
| Glyceraldehyde | 0.1 | 0.0 | 0.0 | 0.0 |
| Lactic acid | 2.6 | 1.6 | 3.3 | 3.6 |
| MeOH | 0.3 | 0.3 | 0.4 | 0.3 |
| EtOH | 2.1 | 1.1 | 1.4 | 7.3 |
| Gas phase product selectivity, % | | | | |
| Methane | 17.1 | 18.3 | 18.3 | 21.2 |
| Ethane | 1.1 | 0.9 | 8.2 | 7.2 |
| Propane | 0.6 | 0.4 | 2.6 | 4.2 |
| n-Butane | 0.2 | 1.2 | 6.4 | 3.6 |
| n-Pentane | 1.2 | 0.6 | 2.1 | 0.2 |
| CO | 3.6 | 1.3 | 0.03 | 0.16 |
| CO$_2$ | 20.9 | 14.3 | 15.5 | 17.3 |
| C deficit, % | −1.82 | 3.84 | 1.85 | 6.6 |

Reaction conditions: Glycerol: 3 g,
5% Ru/Al$_2$O$_3$: 0.125 g,
5% Pt/Al$_2$O$_3$: 0.125 g,
P$_{N2}$: 14 bar,
Solvent: H$_2$O;
Initial liquid volume: 30 mL;
Batch reaction time: 6 h To evaluate the advantage of in situ hydrogen generation for glycerol hydrogenolysis to 1,2-PDO, experiments were performed with 1:1 Ru:Pt admixture catalyst with and without external H$_2$ addition under otherwise identical conditions. The results at 220° C. (493 K) are compared in Table 5.

TABLE 5

Glycerol hydrogenolysis with and without external H$_2$ addition

| | Without external H$_2$ addition (P$_{N2}$: 14 bar) | With externally added H$_2$ (P$_{H2}$: 41 bar) |
|---|---|---|
| Glycerol Conversion, % | 50.2 | 62.8 |
| Liquid phase product selectivity, % | | |
| EG | 6.26 | 11.1 |
| 1,2-PDO | 47.2 | 31.9 |
| Glyceraldehyde | 0.0 | 0.01 |
| Lactic acid | 1.6 | 1.01 |
| MeOH | 0.3 | 0.0 |
| EtOH | 1.1 | 1.0 |
| 2-Propanol | 0.0 | 0.1 |
| Gas phase product selectivity, % | | |
| CH$_4$ | 18.3 | 34.6 |
| C$_2$H$_6$ | 0.9 | 9.3 |
| C$_3$H$_8$ | 0.4 | 5.5 |
| n-C$_4$H$_{10}$ | 1.2 | 0.4 |
| n-C$_5$H$_{12}$ | 0.6 | 0.2 |

TABLE 5-continued

Glycerol hydrogenolysis with and without external $H_2$ addition

|  | Without external $H_2$ addition ($P_{N2}$: 14 bar) | With externally added $H_2$ ($P_{H2}$: 41 bar) |
|---|---|---|
| CO | 1.3 | 1.0 |
| $CO_2$ | 14.3 | 2.4 |
| C deficit, % | 3.84 | 3.07 |

Reaction conditions:
Glycerol: 3 g,
5% $Ru/Al_2O_3$: 0.125 g,
5% $Pt/Al_2O_3$: 0.125 g,
Temp: 493 K;
Solvent: $H_2O$;
Initial liquid volume: 30 mL;
Batch reaction time: 6 h.

The results in Table 5 demonstrate the advantage of in situ hydrogen generation for glycerol hydrogenolysis (1,2-PDO selectivity: 47.2%) over the externally added hydrogen condition (1,2-PDO selectivity: 31.9%). It is important to note that alkane selectivity increased and $CO_2$ selectivity decreased sharply with external hydrogen addition. In this case, more hydrogen (in addition to the in situ generated hydrogen) is available to convert the CO and $CO_2$ to methane and other alkanes. This would shift the equilibrium for further glycerol reforming to CO, and therefore to more undesired gaseous products. The increased ethylene glycol (EG) selectivity with externally added hydrogen also suggests enhanced glycerol reforming (via C—C cleavage) activity.

Figure 6:
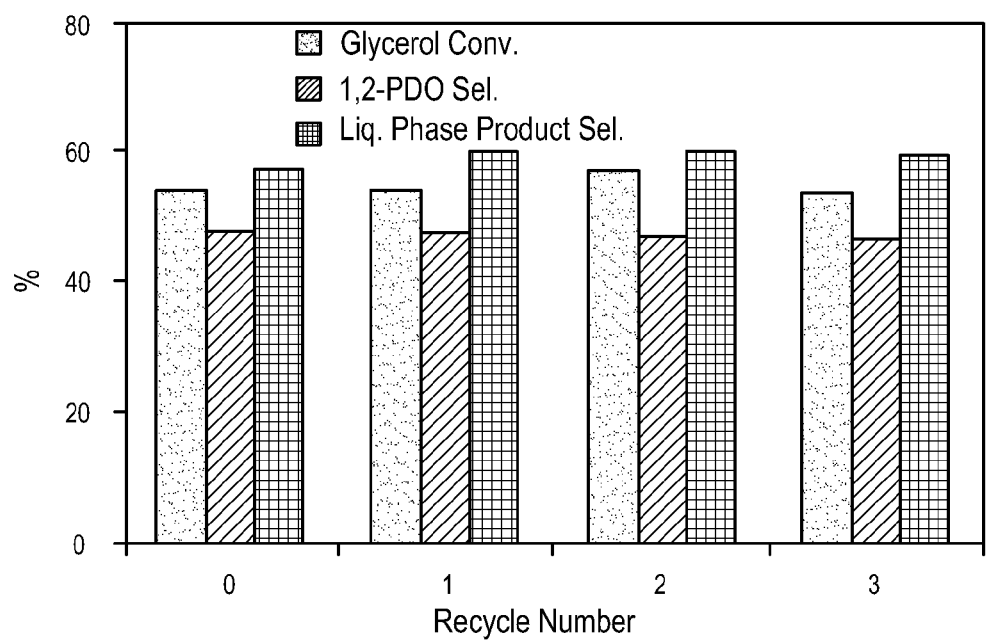
FIG. 6 includes a graph that shows catalyst recycling with 1:1 (wt/wt) 5% Ru/$Al_2O_3$-5% Pt/$Al_2O_3$ admixture catalysts on glycerol hydrogenolysis without externally added hydrogen.

In order to check the stability and reusability of the Ru:Pt admixture catalyst system under the glycerol hydrogenolysis conditions, the catalyst was recycled three times. It was observed that the glycerol conversion as well the total yields of liquid and gas phase products and their compositions remained identical during all the recycle runs within experimental error (FIG. 6) indicating very good catalyst stability and recyclability. We were able to recover ~97% of the catalyst used in the first run. The BET surface areas of the admixture catalyst before and after the recycle studies were nearly identical (170 $m^2$/g and 167 $m^2$/g) indicating that there was no catalyst fouling during the recycle runs. The 1:1 wt/wt 5% $Ru/Al_2O_3$ and 5% $Pt/Al_2O_3$ admixture catalyst is stable, and is useful for performing hydrogenolysis of polyols with no externally added hydrogen.

Additionally, Ru—Re (bimetallic) and Pt admixture catalyst and Ru—Pt—Re (trimetalic) catalyst were studied in comparison to other catalysts for hydrogenolysis of glycerol at: glycerol at 3 g, temperature at 220° C., $P_{N2}$ at 14 bar, solvent is $H_2O$, liquid volume at 30 ml, and time at 6 hours. The results are shown in Table 6. The Ru—Re and Pt admixture catalyst gives highest selectivity to hydrodeoxygenation (HDO) products (71%). The Ru—Pt—Re tri-metallic catalyst can also be used for hydrogenolysis in the absence of externally added hydrogen. HDO products include the lower oxygenated products from any polyol. For example 1,2-PDO and propanol are the lower oxygenated products from glycerol. HDO products can also be referred as hydrogenolysis products.

TABLE 6

| # | Catalyst | Catalyst wt, g | Conv., % | 1,2-PDO sel., % | Propanol sel., % |
|---|---|---|---|---|---|
| 1 | 2% Pt/C | 0.625 | 23.7 | 44.6 | 0.7 |
| 2 | 2% Ru/C | 0.625 | 28.9 | 57.8 | 0.0 |
| 3 | 2% Ru/C | 0.3125 | 39.5 | 55.5 | 0.0 |
|   | 2% Pt/C | 0.3125 |  |  |  |
| 4 | 2% Ru—2% Re/C | 0.3125 | 43.5 | 62.9 | 8.1 |
|   | 2% Pt/C | 0.3125 |  |  |  |
| 5 | 2% Ru—2% Re/C | 0.625 | 44.1 | 43.2 | 2.9* |
| 6 | 2% Pt—2% Re/C | 0.625 | 43.9 | 51.0 | 2.4 |
| 7 | 2% Ru—2% Pt/C | 0.625 | 42.5 | 51.2 | 0.3 |
| 8 | 2% Pt—2% Re/C | 0.3125 | 45.7 | 57.8 | 0.6 |
|   | 2% Ru/C | 0.3125 |  |  |  |
| 9 | 2% Ru—2% Pt—2% Re/C | 0.625 | 58.4 | 53.4 | 1.9 |

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g.,"a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A hydrogenolysis process comprising:
providing a catalytic system comprising platinum metal (Pt), rhenium metal (Re), and ruthenium metal (Ru);
reacting glycerol with the catalyst system to produce hydrogen in situ and intermediates formed from glycerol; and
reacting the in situ formed hydrogen and the intermediates with the catalyst system to form 1,2-propanediol.

2. The process of claim 1, wherein the catalytic system is held at a temperature of 180° C. to 250° C. at which the reactions occur.

3. The process of claim 1, wherein the catalytic system is a solid catalyst in contact with a liquid either as a packing or a suspension and the reactions occur in the liquid.

4. The process of claim 1, wherein the reaction occurs without external hydrogen.

5. The process of claim 1, wherein said process has a conversion from about 20% to about 83%.

6. The process of claim 1, wherein said process has a selectivity of more than 53 mole % for 1,2-propanediol.

7. The hydrogenolysis process of claim 1, wherein the catalytic system has a synergistic catalytic potential for hydrogenolysis of the glycerol.

8. The hydrogenolysis process of claim 1 wherein the catalytic system is selected from the group consisting of (a) a Ru—Re bimetallic and Pt admixture and (b) a Ru—Pt—Re trimetallic catalyst.

9. The hydrogenolysis process of claim 1 wherein the catalytic system comprises about 2% Ru, about 2% Pt, and about 2% Re.

10. A reaction system comprising:
a catalyst combination of platinum metal (Pt), rhenium metal (Re), and ruthenium metal (Ru); and
a polyol.

11. The reaction system of claim 10, wherein the polyol is selected from the group consisting of glycerol, glucose, sorbitol, mannitol, fructose, cellobiose, a polyhydroxy compound, and combinations thereof.

12. The reaction system of claim 11, further comprising water.

13. The reaction system of claim 12, wherein said polyol has a polyol content ranging from about 0.001 to about 99.99% of the liquid phase composition exclusive of the catalyst.

14. The reaction system of claim 10 wherein there is an absence of externally added hydrogen.

15. The reaction system of claim 10, further comprising in situ formed hydrogen in the absence of externally added hydrogen.

16. The reaction catalytic system of claim 15, wherein said catalyst is in contact with a liquid either as a packing or a suspension.

17. The reaction system of claim 10 wherein the polyol is glycerol.

* * * * *